(12) United States Patent
Greenwald

(10) Patent No.: US 8,658,193 B2
(45) Date of Patent: Feb. 25, 2014

(54) STYPTIC STORAGE AND DELIVERY

(76) Inventor: Robert J. Greenwald, Venice, FL (US)

( * ) Notice: Subject to any disclaimer, the term of this patent is extended or adjusted under 35 U.S.C. 154(b) by 8 days.

(21) Appl. No.: 13/492,766

(22) Filed: Jun. 8, 2012

(65) Prior Publication Data

US 2013/0330416 A1    Dec. 12, 2013

(51) Int. Cl.

| | |
|---|---|
| *A01N 25/00* | (2006.01) |
| *A01N 25/08* | (2006.01) |
| *A61K 9/50* | (2006.01) |
| *A01N 59/00* | (2006.01) |
| *A61K 33/00* | (2006.01) |
| *A01N 59/16* | (2006.01) |
| *A61K 33/26* | (2006.01) |
| *A01N 59/06* | (2006.01) |
| *A61K 33/08* | (2006.01) |
| *A61K 33/06* | (2006.01) |
| *A61K 33/38* | (2006.01) |
| *A01N 59/02* | (2006.01) |
| *A61K 33/04* | (2006.01) |
| *A01N 65/00* | (2009.01) |
| *A61K 36/10* | (2006.01) |
| *A01N 55/02* | (2006.01) |
| *A61K 31/28* | (2006.01) |
| *A01N 55/06* | (2006.01) |
| *A61K 31/31* | (2006.01) |
| *A61K 31/295* | (2006.01) |
| *A01N 27/00* | (2006.01) |
| *A61K 31/01* | (2006.01) |

(52) U.S. Cl.
USPC ........... 424/405; 424/409; 424/502; 424/600; 424/647; 424/618; 424/682; 424/685; 424/688; 424/698; 424/709; 424/718; 424/722; 424/762; 424/DIG. 5; 514/495; 514/497; 514/502; 514/762

(58) Field of Classification Search
USPC .......... 424/405, 409, 600, 502; 514/495, 497, 514/502
See application file for complete search history.

(56) References Cited

U.S. PATENT DOCUMENTS

| | | |
|---|---|---|
| 3,641,239 A | 11/1968 | Mohrlok |
| 4,166,108 A | 8/1979 | Brown et al. |
| 5,575,995 A * | 11/1996 | Giovanoni ................. 424/78.06 |
| 5,955,112 A * | 9/1999 | Kaplan ........................ 424/682 |
| 2003/0153528 A1* | 8/2003 | Levinson ........................ 514/54 |
| 2003/0165560 A1 | 9/2003 | Otsuka et al. |
| 2004/0191317 A1* | 9/2004 | Kaplan ........................ 424/486 |
| 2007/0104666 A1 | 5/2007 | Haltom |
| 2010/0255131 A1* | 10/2010 | Kanaujia et al. .............. 424/744 |

* cited by examiner

*Primary Examiner* — Mina Haghighatian
*Assistant Examiner* — Helen Chui
(74) *Attorney, Agent, or Firm* — Long Technology Law, LLC; Joseph Long

(57) ABSTRACT

Technologies are described herein for styptic compounds comprising a hemostatic or styptic agent suspended within a hydrophobic carrier medium. Example carrier mediums may include waxes, lipids, oils, or combinations thereof. The compound may be a semisolid at room temperature and soft enough to be easily dispensed and formed into or onto bleeding tissue of an animal or human. The hydrophobic qualities of the carrier medium can protect the styptic agent from absorbing moisture. The carrier medium can mechanically support positioning treatments adjacent to the bleeding tissue. The carrier medium can further serve to mechanically seal the tissue to aid in hemostasis while also protecting the tissue from debris and contamination. The carrier medium can aid in maintaining moisture within the tissue. Slurry-based manufacturing processes can support a substantially homogeneous dispersal of styptic agent throughout the carrier medium.

10 Claims, 4 Drawing Sheets

STYPTIC STORAGE AND DELIVERY

BACKGROUND

Bleeding from cut or nicked animal tissue is common in various minor medical or veterinary procedures as well as everyday life. Veterinary examples include trimming nails, beaks, wings, tails, ears, and so forth. Human tissue examples include shaving nicks, kitchen mishaps, and dermatological procedures. Styptic or hemostatic materials may be applied to these biological tissues to aid in the control of bleeding.

Traditional styptic material is generally provided as a powder or a pencil. The powder is well known to be messy and cumbersome to apply. For example, veterinarians find it difficult to place and hold a messy powder into a cut nail or other tissue of a moving animal. The powders often simply fall away from the tissue once put into place. Styptic pencils are merely styptic powder compressed into a pencil or crayon shape. These are generally hard like a stone and must be scratched into a powder or applied with water for the active ingredients to engage into the tissue.

Styptic materials generally absorb water easily. Absorbing water, even from humid air, causes styptic powders to solidify into a solid or crumbling cake or rock. Similarly, absorbed water causes styptic pencils to deform, crumble, or both. Despite water having such a negative effect on the storage and use of styptic materials, instructions for styptic powders or pencils often suggest moistening the material prior to application in order to soften or disperse the ingredients into the tissue.

There is a long felt need to simplify the application of styptic agents and also to protect the styptic agents from absorbing water during use and storage. It is with respect to these considerations and others that the disclosure made herein is presented.

SUMMARY

Technologies are described herein for compounds comprising a hemostatic or styptic agent suspended in a hydrophobic carrier medium such as a wax, lipid, oil, or combination thereof. The compound may be a semisolid at room temperature and soft enough to be easily dispensed and formed into or onto bleeding tissue of an animal or human. The hydrophobic qualities of the carrier medium can protect the styptic agent from absorbing moisture. The carrier medium can mechanically support positioning styptic agents, other medications, or other treatments adjacent to the bleeding tissue. The carrier medium can further serve to mechanically seal the tissue to aid in hemostasis while also protecting the tissue from debris and contamination. The carrier medium can aid in maintaining moisture within the tissue. Slurry-based manufacturing processes can support a substantially homogeneous dispersal of styptic agent throughout the carrier medium.

It should be appreciated that the above-described subject matter may also be implemented as an apparatus, a system, a treatment process, a manufacturing process, or as an article of manufacture. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
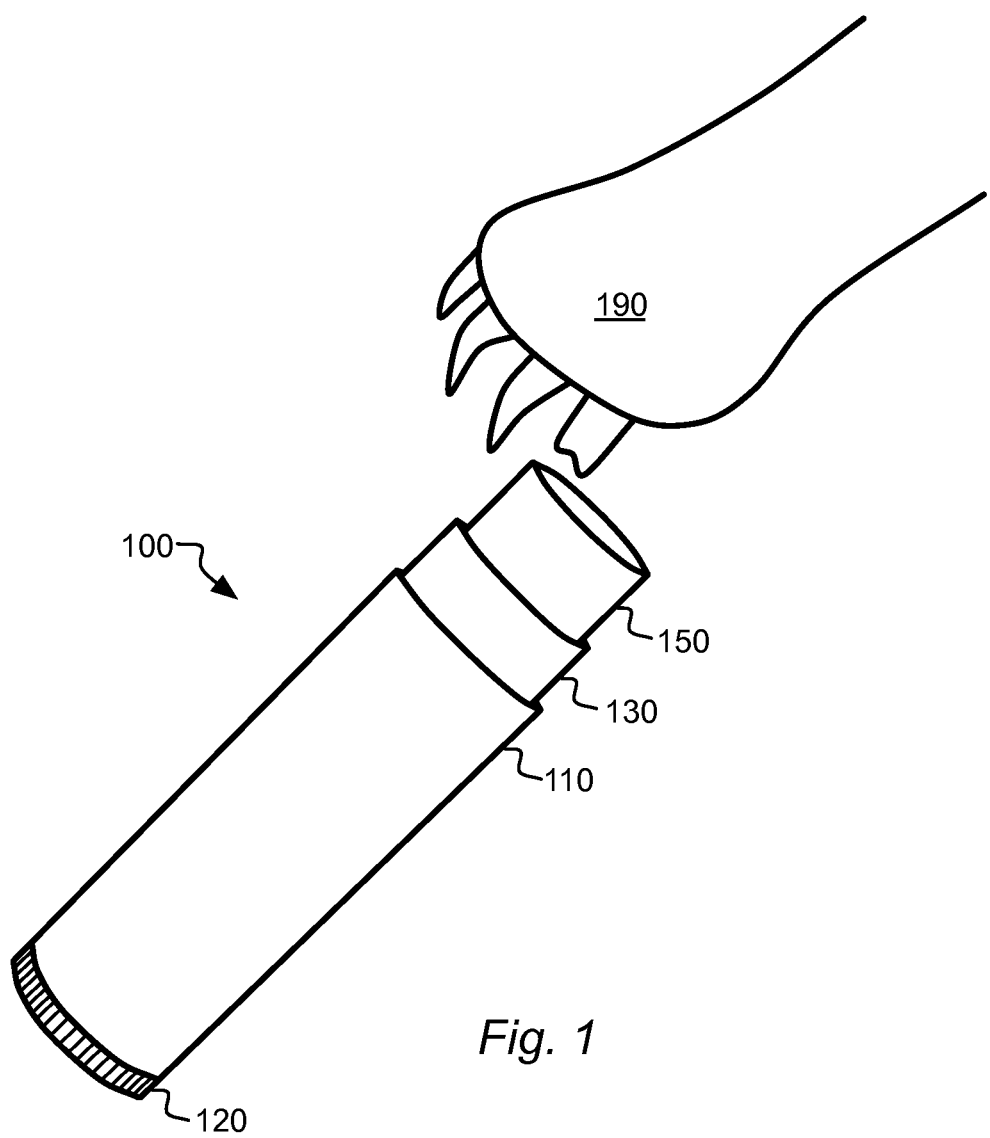
FIG. 1 is a schematic diagram illustrating a styptic device according to one or more embodiments presented herein.

The following description is directed to technologies for compounds comprising hemostatic or styptic agent suspended in a hydrophobic carrier medium. In the following detailed description, references are made to the accompanying drawings that form a part hereof, and which are shown by way of illustration specific embodiments or examples. Referring now to the drawings, in which like numerals represent like elements throughout the several figures, aspects of the inventive technology will be presented.

Turning first to FIG. 1, a schematic diagram illustrates a styptic device 100 according to one or more embodiments presented herein. The styptic device 100 includes a styptic compound 150. The styptic compound 150 may be provided within a dispenser. The dispenser may include an elongated hollow tube 110 within which the styptic compound 150 may be provided. The open end of the tube 110 may incorporate a recess 130 for affixing a cap (not illustrated here). The cap may be operable to cover the styptic compound 150 for storage. The closed end of the tube 110 may include a dial 120 for moving the styptic compound 150 along the center axis of the tube 110. The styptic compound 150 may be applied to a biological tissue 190 such as the illustrated animal claw example.

The styptic compound 150 may treat various biological tissues 190. The biological tissues 190 may relate to various veterinary examples. One veterinary example includes trimming animal nails too closely where living tissue may be found within the center of the nail such as in dogs, cats, rabbits, birds, and other animals. Other veterinary examples include the trimming of beaks, wings, tails, horns, ears, and so forth. The biological tissues 190 may also relate to various human examples. Human tissue examples include shaving nicks, kitchen mishaps, dermatological procedures, first-aid, or various other medical procedures.

The styptic compound 150 may include one or more styptic agents suspended within a hydrophobic carrier medium. Composition of the styptic compound 150 is addressed in further detail with respect to FIG. 2 below.

The styptic device 100 may include the styptic compound 150 provided within a dispenser. According to one or more embodiments, the dispenser may include a hollow tube 110 operable to contain the styptic compound 150. A dial 120 positioned on or within the tube 110 may be operated to extend or retract the styptic compound 150 along the center axis of the tube 110 and out through the open end of the tube 110. The dial 120, or other operating mechanism, may engage with the styptic compound 150 within the tube 110 using a screw-like mechanism, a plunger, or some other actuation mechanism such as pushing, squeezing, extruding, or so forth.

While the example embodiment of the styptic device 100 illustrated herein incorporates a tube 110 in the dispenser structure, it should be appreciated that various other embodiments may use other dispenser structures without departing from the scope or spirit of the technology presented herein. Examples of dispenser structures may include an ointment tin, a paste tube, a single portion container, a foil pouch, a vial, a bottle, a wrapped stick, a tub, a jar, or any other container for storing and dispensing the styptic compound 150.

Figure 2:
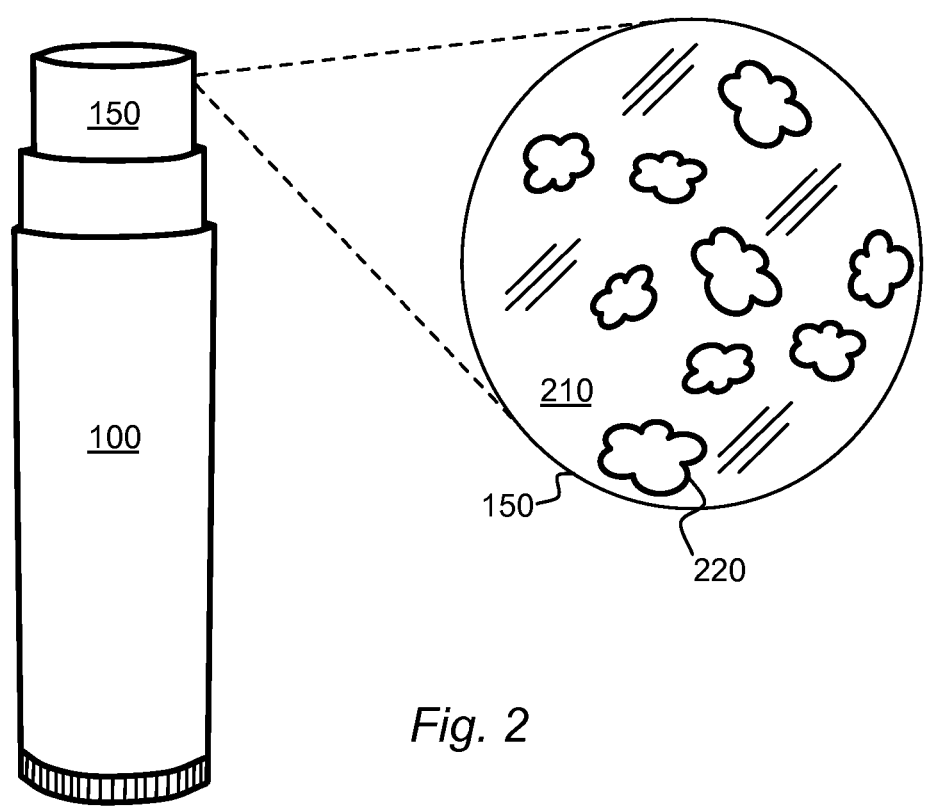
FIG. 2 is a schematic diagram illustrating a styptic device with a close-up of a styptic compound according to one or more embodiments presented herein.

Turning now to FIG. 2, a schematic diagram illustrates a styptic device 100 with a close-up of a styptic compound 150 according to one or more embodiments presented herein. The close-up view of the styptic compound 150 shows particles 220 of active ingredient suspended within a carrier medium 210.

The particles 220 may include styptic or hemostatic agents. The styptic agents may act to contract or astringe blood vessels in biological tissues 190. Such styptic agents may work by causing vasoconstriction or by promoting platelet aggregation within biological tissues 190. According to one or more embodiments, the particles 220 may include other active ingredients, chemicals, drugs, or treatments.

The styptic agents associated with the particles 220 may include ferric subsulfate, other iron compounds, silver nitrate, other silver compounds, aluminum sulfate, aluminum chloride, potassium alum, other forms of alum, other aluminum compounds, titanium dioxide, or other titanium compounds. Generally, the styptic agents may include any chemical or compound operable to stanch blood by causing blood vessels to contract within biological tissues 190. Similarly, the styptic agents may include any chemical or compound operable to promote flocculation of the blood within biological tissues 190 according to a high ionic strength associated with the chemical or compound.

The styptic agents associated with the particles 220 may include collagen. For example, microfibrillar collagen hemostat (MCH) may be used to attract platelets and promote blood clotting. Similarly, the styptic agents associated with the particles 220 may include chitosan, chitosan salts, chitin, or diatomaceous material. Chitosan may be used to bond with platelets and red blood cells to form a gel-like clot capable of sealing bleeding vessels.

The styptic agents associated with the particles 220 may include herbal, plant, or traditional remedies. For example, such treatments associated with reduction in bleeding may include baibaodan, yunnan baiyao, white medicinal powder, myrrh, dragon's blood, other plant resins, other plant astringents, or any combination thereof.

The carrier medium 210 may include a lipid, wax, oil, or any combination thereof. The carrier medium 210 may include any hydrophobic material safe for application to the biological tissue 190. The carrier medium 210 may include soy wax, paraffin wax, bee's wax, palm wax, other waxes, oils, petrolatum, various other lipids, or any combination thereof. According to various embodiments, the carrier medium 210 may include stearic acid, aloe vera gel, mineral oil, plant oils, animal oils, polyethylene glycol, various polymers, polyethers, or any combination thereof.

Materials, or combinations of materials, as suggested for the carrier medium 210 are generally hydrophobic. These hydrophobic materials within the carrier medium 210 may serve to protect the particles 220 from water and moisture.

According to one or more embodiments, the carrier medium 210 may have a waxy or gel-like consistency allowing the styptic compound 150 to form against, form within, form to, coat, seal, or gently adhere to the application site of the biological tissue 190. Adjusting related properties of the carrier medium 210 can provide a styptic compound 150 operable of some, or all, of at least five separate functions. Firstly, the carrier medium 210 can protect the particles 220 from water or moisture during storage and application. Second, the carrier medium 210 can support physically positioning the particles 220 adjacent to the biological tissue 190. Third, the carrier medium 210 can mechanically seal against the biological tissue 190 to further aid hemostasis. Fourth, the carrier medium 210 can mechanically seal the biological tissue 190 against debris or contamination during the healing process. Fifth, the carrier medium 210 can seal moisture into the biological tissue 190 to prevent over-drying during the healing process.

It should be appreciated that the carrier medium 210 may be mixed to have various operating consistencies. Some examples may include the consistency of a wax, gel, ointment, paste, salve, or so forth. According to various embodiments, the consistency of the carried medium 210 and resulting styptic compound 150 may be specified or designed to match the structure, or various geometries, of a dispenser or applicator. According to one or more embodiments, the carrier medium 210 may be firm enough at ambient operating temperatures to remain a solid or semisolid and support application in a stick form. Such a stick form may be dispensed from a tube 110 as depicted in the illustrated example.

Figure 3:
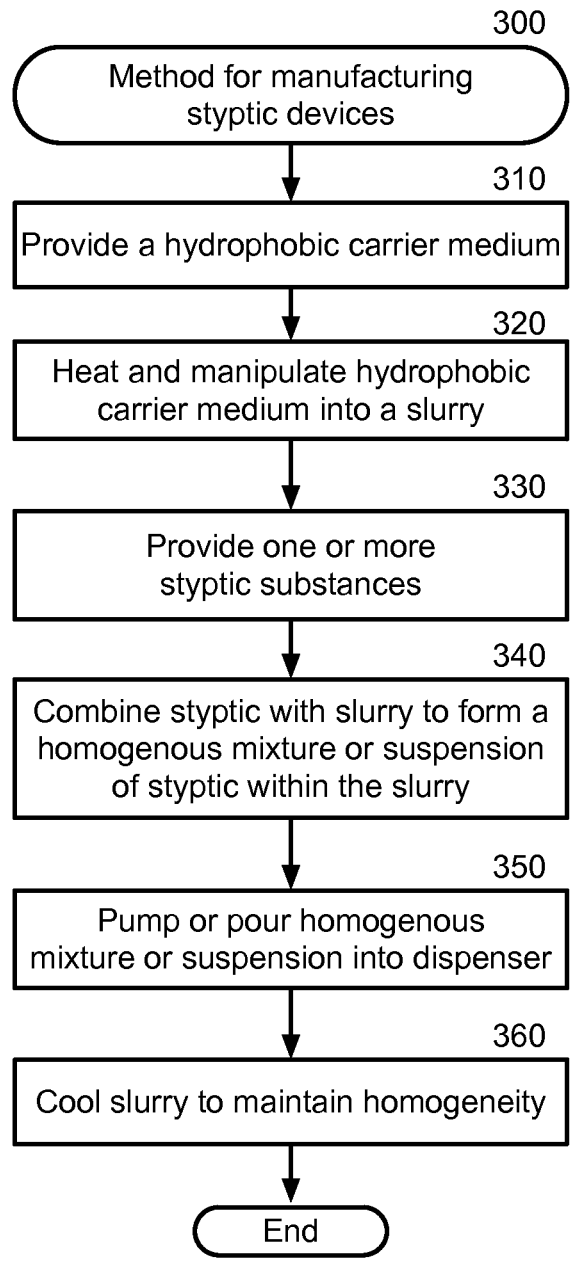
FIG. 3 is a block flow diagram depicting a method for manufacturing styptic devices according to one or more embodiments presented herein.

Turning now to FIG. 3, a block flow diagram depicts a method 300 for manufacturing styptic devices 100 according to one or more embodiments presented herein. The method 300 is described with reference to the elements illustrated in FIG. 1 and FIG. 2.

In block 310, a carrier medium 210 may be provided. One or more materials may be provided for forming a carrier medium 210. The one or more materials may combine to form a carrier medium 210 that is substantially hydrophobic.

In block 320, the carrier medium 210 may be heated and/or manipulated into a slurry. The manipulation may include pumping, stirring, extruding, kneading, compressing, twisting, folding, and other mechanical manipulation, or any combination thereof. The manipulation may also serve to combine the one or more materials provided for forming the carrier medium 210 in block 310. The heating and/or manipulation may be specified or designed to achieve a desired thickness, consistency, or viscosity of the slurry. These qualities may be specified to support other manufacturing steps. These qualities may be specified to support the desired suspension of particles 220 as discussed with respect to block 340.

In block 330, one or more styptic agents may be provided. The styptic agents may be provided as all, or part, of the particles 220 of active ingredients.

In block 340, the styptic agents may be combined into the slurry. The styptic agents may be combined as all, or part, of the particles 220 of active ingredients. The particles 220 may be combined into the slurry to form a homogenous mixture or suspension of particles 220 within the slurry.

In block 350, the homogenous mixture or suspension may be pumped, poured, or otherwise transferred into dispensers. The dispensers may have various structures or geometries. Some example dispenses may incorporate a structure of a tube 110. The dispenser may also serve as an applicator.

In block 360, the slurry may be cooled to maintain homogeneity of the particles 220 within the carrier medium 210. The cooling may be active or passive. The dispensers may be moved or agitated during the cooling process to aid in maintaining homogeneity of the styptic compound 150.

After block 360, the method 300 ends. Of course, additional styptic devices 100 may continue to be manufactured according to the method 300.

Figure 4:
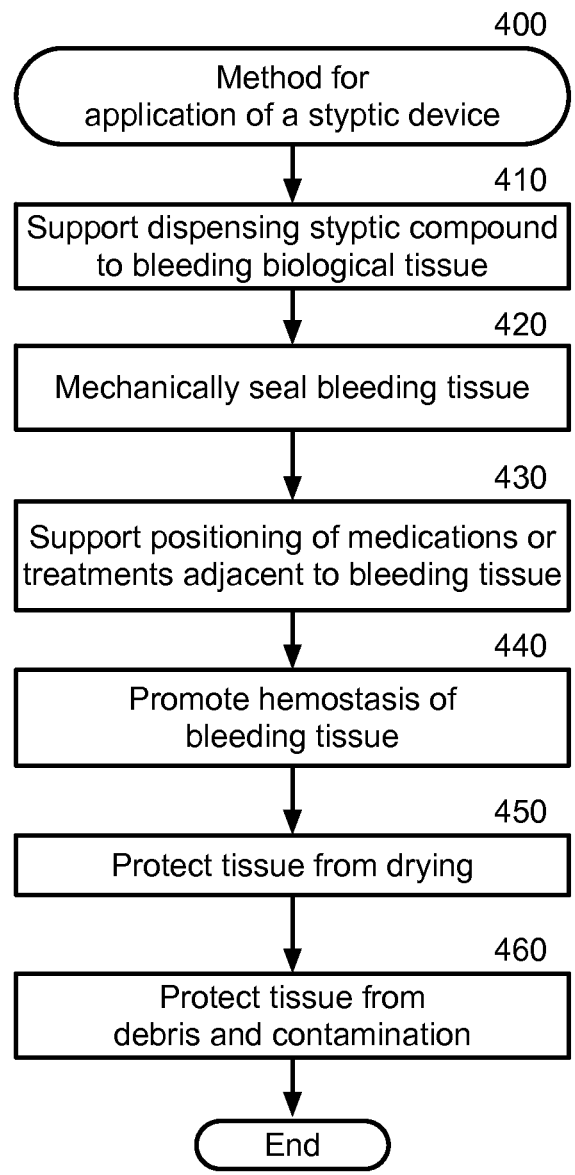
FIG. 4 is a block flow diagram depicting a method for application of a styptic device according to one or more embodiments presented herein.

Turning now to FIG. 4, a block flow diagram depicts a method 400 for application of a styptic device according to one or more embodiments presented herein. The method 400 is described with reference to the elements illustrated in FIG. 1 and FIG. 2.

In block 410, a styptic compound 150 is dispensed into bleeding biological tissue 190. The styptic compound 150 may be dispensed directly from a dispenser/applicator or indirectly from a dispenser using a finger, swab, or other instrument.

In block 420, the styptic compound 150 can mechanically seal the bleeding tissue 190. The consistency of the styptic compound 150 may aid in forming to, coating, or gently adhering to the tissue 190.

In block 430, the styptic compound 150 can support positioning of medications or treatments adjacent to bleeding tissue 190. The medications or treatments may be suspended within the styptic compound 150 as particles 220. The medications or treatments may include one or more styptic agents. Other treatments may be included within the particles 220 such as antibiotics, pain relievers, and so forth.

In block 440, the styptic compound 150 can promote hemostasis of the bleeding tissue. The promotion of hemostasis may include a chemical effect associated with the styptic agents or other active ingredients within the particles 220. The promotion of hemostasis may include a mechanical effect associated with the sealing discussed with respect to block 420.

In block 450, the styptic compound 150 can protect the tissue 190 from drying out or dehydrating. This protection may be associated with the sealing discussed with respect to block 420.

In block 460, the styptic compound 150 can protect tissue from debris and contamination. This protection may be associated with the sealing discussed with respect to block 420.

After block 460, the method 400 ends. Of course, additional applications of styptic devices 100 may continue according to the method 400.

The exemplary methods and blocks described in the embodiments presented previously are illustrative, and, in alternative embodiments, certain blocks can be performed in a different order, in parallel with one another, omitted entirely, and/or combined between different exemplary methods, and/or certain additional blocks can be performed, without departing from the scope and spirit of the invention. Accordingly, such alternative embodiments are included in the invention described herein.

Based on the foregoing, it should be appreciated that technologies for styptic devices are presented herein. Although the subject matter presented herein has been described in specific language related to structural features or methodological acts, it is to be understood that the invention defined in the appended claims is not necessarily limited to the specific features or acts described herein. Rather, the specific features and acts are disclosed as example forms of implementation.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. A treatment system comprising:
    a hydrophobic carrier medium consisting of soy wax and petrolatum, and particles of a styptic material to form a homogeneous mixture or suspension devoid of water; and
    a dispenser operable to dispense the mixture or suspension to a biological tissue;
    wherein the hydrophobic carrier medium is operable to mechanically seal the biological tissue and to protect the particles of styptic material from absorbing water and moisture during storage and application, and wherein the particles of styptic material are operable to astringe blood vessels within the biological tissue to reduce bleeding.

2. The treatment system of claim 1, wherein the styptic material comprises ferric subsulfate.

3. The treatment system of claim 1, wherein the styptic material comprises one or more of chitosan, chitosan salt, and chitin.

4. The treatment system of claim 1, wherein the dispenser is in the form of a tube.

5. A method for manufacturing a styptic device, the method comprising:
    heating and manipulating a hydrophobic carrier medium consisting of soy wax and petrolatum into a slurry;
    combining particles of a styptic material into the slurry to form a homogenous mixture or suspension devoid of water;
    transferring the mixture or suspension into a dispenser; and
    cooling the mixture or suspension within the dispenser.

6. The method of claim 5, wherein the styptic material comprises one or more of aluminum sulfate, aluminum chloride, potassium alum, silver nitrate and titanium dioxide.

7. The method of claim 5, wherein the dispenser is in the form of a tube.

8. The method of claim 5, wherein manipulating the hydrophobic carrier medium comprises pumping, stirring, kneading or folding.

9. The method of claim 5, wherein the styptic material comprises ferric subsulfate.

10. The method of claim 5, wherein the styptic material comprises one or more of chitosan, chitosan salt, and chitin.

* * * * *